United States Patent
Tate et al.

(10) Patent No.: US 9,907,735 B2
(45) Date of Patent: Mar. 6, 2018

(54) EXTERNAL COMPOSITION FOR SKIN

(71) Applicant: ROHTO PHARMACEUTICAL CO., LTD., Osaka-shi, Osaka (JP)

(72) Inventors: Yumiko Tate, Osaka (JP); Shun Kimura, Osaka (JP)

(73) Assignee: ROHTO PHARMACEUTICAL CO., LTD., Osaka-Shi (JP)

( * ) Notice: Subject to any disclaimer, the term of this patent is extended or adjusted under 35 U.S.C. 154(b) by 0 days.

(21) Appl. No.: 15/520,738

(22) PCT Filed: Oct. 20, 2015

(86) PCT No.: PCT/JP2015/079510
§ 371 (c)(1),
(2) Date: Apr. 20, 2017

(87) PCT Pub. No.: WO2016/063847
PCT Pub. Date: Apr. 28, 2016

(65) Prior Publication Data
US 2017/0304167 A1    Oct. 26, 2017

(30) Foreign Application Priority Data

Oct. 21, 2014 (JP) ................................. 2014-214564

(51) Int. Cl.
    *A61K 8/00*      (2006.01)
    *A61K 8/18*      (2006.01)
    *A61K 38/00*      (2006.01)
    *A61K 8/26*      (2006.01)
    *A61Q 1/12*      (2006.01)
    *A61K 8/34*      (2006.01)
    *A61K 8/35*      (2006.01)
    *A61K 8/49*      (2006.01)
    *A61K 8/46*      (2006.01)
    *A61K 8/24*      (2006.01)
    *A61K 8/29*      (2006.01)
    *A61Q 19/00*      (2006.01)

(52) U.S. Cl.
CPC ............... *A61K 8/347* (2013.01); *A61K 8/24* (2013.01); *A61K 8/26* (2013.01); *A61K 8/29* (2013.01); *A61K 8/35* (2013.01); *A61K 8/466* (2013.01); *A61K 8/49* (2013.01); *A61Q 19/00* (2013.01); *A61K 2800/40* (2013.01)

(58) Field of Classification Search
None
See application file for complete search history.

(56) References Cited

U.S. PATENT DOCUMENTS

2011/0250250 A1* 10/2011 Kishida ................ A61K 8/0241
                                                                                                 424/401

FOREIGN PATENT DOCUMENTS

| JP | 3-284613 A | 12/1991 |
| JP | 5-117127 A | 5/1993 |
| JP | 10-330209 A | 12/1998 |
| JP | 2011-236202 A | 11/2011 |
| JP | 2014-5256 A | 1/2014 |
| JP | 2014-91741 A | 5/2014 |

OTHER PUBLICATIONS

Machine translation for IDS reference JP2014-005256 (A); downloaded Aug. 29, 2017; published Jan. 16, 2014.*
Machine translation for JP 2014005256A; published Jan. 16, 2014.*
Inoue et al., "Synthesis and Property of the Mn Doped Oxide Red Phosphors in the Calcium Aluminates", Mie-Ken Kogyo Kenkyusho Kenkyu Hokoku, 2011, No. 35.
International Search Report for PCT/JP2015/079510 (PCT/ISA/210) dated Jan. 26, 2016.
Written Opinion of the International Searching Authority for PCT/JP2015/079510 (PCT/ISA/237) dated Jan. 26, 2016.

* cited by examiner

*Primary Examiner* — Jeffrey T. Palenik
(74) *Attorney, Agent, or Firm* — Birch, Stewart, Kolasch & Birch, LLP

(57) ABSTRACT

An object of the present invention is to provide an external composition for skin excellent in ultraviolet-ray absorbability. The present invention relates to the external composition for skin comprising (a) an ultraviolet-ray absorber, and (b) an inorganic phosphor. (a) The ultraviolet-ray absorber preferably contains at least one ultraviolet-ray absorber which absorbs UVB. Also, (a) the ultraviolet-ray absorber is more preferably at least one ultraviolet-ray absorber selected from the group consisting of 2-ethylhexyl paramethoxycinnamate, phenylbenzimidazole sulfonic acid, etc.

7 Claims, 4 Drawing Sheets

Fig. 5-(a)
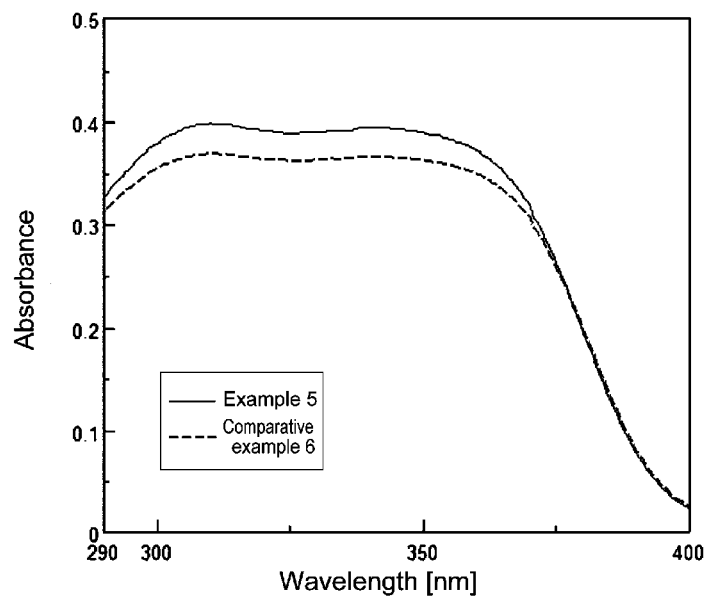
Fig. 5-(b)
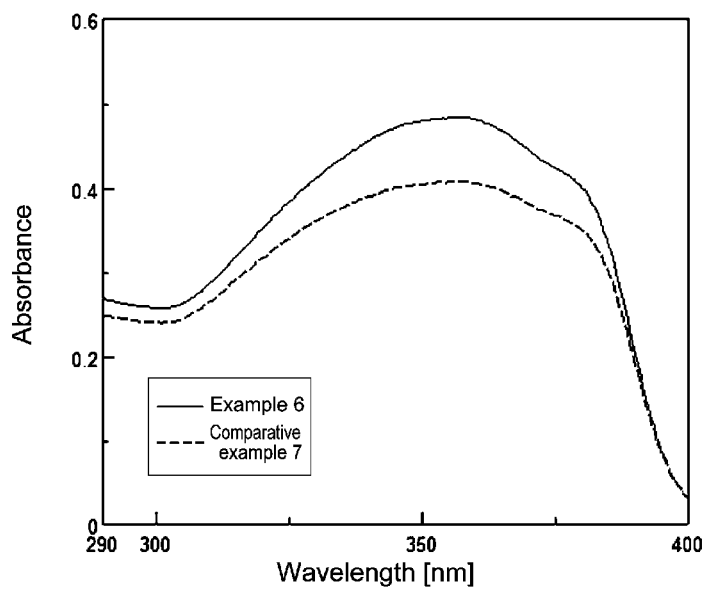

EXTERNAL COMPOSITION FOR SKIN

TECHNICAL FIELD

The present invention relates to an external composition for skin.

BACKGROUND ART

Sunburn occurs when light (ultraviolet-ray) particularly in the ultraviolet region (200 to 400 nm), such as sunlight, artificial light, etc., attacks the skin. It has been said that sunburn is a cause of skin disorders such as erythema, blisters, burns and eventually skin cancer.

The ultraviolet-ray are classified to UV-A (wave A ultraviolet-ray; 320 to 400 nm), UV-B (wave B ultraviolet-ray; 280 to 320 nm), and UV-C (wave C ultraviolet-ray; 200 to 280 nm) depending on the wavelength region. Among these, UV-C is almost absorbed by the ozone layer before it reaches the surface of the earth, so most of the ultraviolet-rays reaching the ground are UV-A and UV-B. UV-A and UV-B have various effects on human skin, but the phenomenon which appears the most conspicuously is sunburn. Sunburn by UV-B is called sunburn which mainly causes inflammatory symptoms such as formation of erythema and blisters on the skin, etc., and sunburn by UV-A is called suntan which causes browning of the skin and induces an abrupt aging phenomenon by promoting lowering of elasticity of the skin and occurrence of wrinkles. It has also been known that UV-A promotes the initiation of erythema reaction, but this erythema response may be enhanced for some kinds of patients, thereby phototoxicity or photoallergic reaction may be caused in some cases.

Cosmetics such as sunscreen cream containing the ultraviolet-ray absorber have been commercially available to prevent such harmful effects by ultraviolet-ray. In order to avoid the damage caused by ultraviolet-ray, it is effective to properly select and use the ultraviolet-ray absorber depending on the purposes, and an UV-A absorbent and an UV-B absorbent are formulated by optionally selecting these in the conventional cosmetics. In recent years, cosmetics, etc., having higher ultraviolet-ray absorption property have been desired, and in view of such circumstances, the applicant of this application has also proposed an external composition for skin enhanced in ultraviolet-ray absorbability (Patent document 1). In such a situation, the external composition for skin which can further enhance the ultraviolet-ray absorbability has been required.

PRIOR ART DOCUMENT

Patent Document

Patent document 1: JP 2014-91741A

SUMMARY OF THE INVENTION

Problem to be Solved by the Invention

An object of the present invention is to provide a novel external composition for skin in which ultraviolet-ray absorbability has been enhanced.

Means to Solve the Problem

The present inventors have intensively studied to solve the above-mentioned problem, and as a result, they have found that, ultraviolet-ray absorbability can be markedly enhanced by formulating an inorganic phosphor and the ultraviolet-ray absorber into an external composition for skin.

That is, the gist of the present invention is as follows.

<1> An external composition for skin which comprises (a) an ultraviolet-ray absorber, and (b) an inorganic phosphor.

<2> The external composition for skin described in <1>, wherein (a) the ultraviolet-ray absorber contains at least one kind of an ultraviolet-ray absorber which absorbs UVB.

<3> The external composition for skin described in <1> or <2>, wherein (a) the ultraviolet-ray absorber is at least one kind of an ultraviolet-ray absorber selected from the group consisting of 2-ethylhexyl paramethoxycinnamate, phenyl-benzimidazole sulfonic acid, isopropyl methoxycinnamate, octyl methoxycinnamate, para-amino-benzoic acid, ethyl PABA, ethyl-dihydroxypropyl PABA, ethylhexyl-dimethyl PABA, homosalate, ethylhexyl salicylate, 3-benzylidene camphor, 4-methylbenzylidene camphor, benzylidene camphor sulfonic acid, camphor benzalkonium methosulfate, polyacrylamidomethyl benzylidene camphor, diethylhexyl butamidotriazone, octyl triazone, disodium phenyl dibenzimidazole tetrasulfonate, a polyorganosiloxane having a benzalmalonate functional group, 4-tert-butyl-4-methoxy-benzoylmethane, hexyl 2-[4-(diethylamino)-2-hydroxybenzoyl]benzoate, 2-(2'-hydroxy-5'-methylphenyl)-benzotriazole, 2-[4,6-bis(2,4-dimethylphenyl)-1,3,5-triazin-2-yl]-5-[(octyl)oxy]-phenol, 2-ethylhexyl dimethoxybenzylideneoxoimidazolidine propionate, 6-(4-methoxyphenyl)-1,3,5-triazine, tetrahydroxybenzophenone, 2-hydroxy-4-methoxybenzophenone, 2,4-bis-[{4-(2-ethylhexyloxy)-2-hydroxy}-phenyl]-drometrizole trisiloxane, 2,2'-methylene-bis[6-(2H-benzotriazole-2-yl)-4-(1,1,3,3-tetramethylbutyl)phenol] and octocrylene.

<4> The external composition for skin described in any of <1> to <3>, wherein (b) the inorganic phosphor is aluminate phosphor.

<5> The external composition for skin described in <4>, wherein the aluminate phosphor is an alkaline earth metal aluminate phosphor.

<6> The external composition for skin described in <5>, wherein the alkaline earth metal aluminate phosphor is calcium manganese aluminate.

<7> The external composition for skin described in <6>, wherein the calcium manganese aluminate is represented by the following formula (1);

$$Ca_XAl_YO_{(2X+3Y+4Z)/2}:Mn^{4+}{}_Z \qquad (1)$$

wherein $0.1<X<1.05$, $11.9<Y\leq12$, and $0.0005<Z<0.1$.

<8> The external composition for skin described in any of <1> to <7>, wherein (a) the ultraviolet-ray absorber contains 2-ethylhexyl paramethoxycinnamate.

<9> The external composition for skin described in any of <1> to <8>, wherein (a) the ultraviolet-ray absorber contains 2-ethylhexyl paramethoxycinnamate and hexyl 2-[4-(diethylamino)-2-hydroxybenzoyl]benzoate.

<10> The external composition for skin described in any of <1> to <9>, wherein a content of (b) the inorganic phosphor is 0.1 to 10% by mass based on the whole external composition for skin.

<11> The external composition for skin described in any of <1> to <10>, wherein it is a sunscreen composition.

Effect of the Invention

According to the present invention, a novel external composition for skin in which ultraviolet-ray absorbability has further enhanced can be provided.

BRIEF EXPLANATION OF THE DRAWINGS

FIG. 5(a) is a drawing showing ultraviolet-ray absorbability of the external composition for skin which is an embodiment of the present invention.

FIG. 5(b) is a drawing showing ultraviolet-ray absorbability of the external composition for skin which is an embodiment of the present invention.

EMBODIMENTS TO CARRY OUT THE INVENTION

Figure 1:
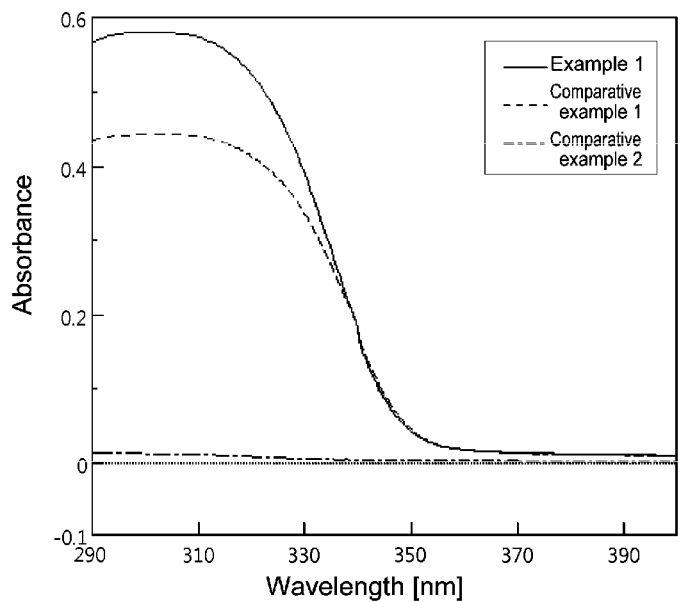
FIG. 1 is a drawing showing ultraviolet-ray absorbability of the external composition for skin which is an embodiment of the present invention.

In the following, the present invention is explained in detail.

[External Composition for Skin]

The external composition for skin of the present invention comprises (a) an ultraviolet-ray absorber, and (b) an inorganic phosphor. In addition, the external composition for skin of the present invention may contain other component(s) within the range which does not impair the effect of the present invention other than the essential components. In the following, these respective components are explained.

<(a) Ultraviolet-Ray Absorber>

(a) The ultraviolet-ray absorber is a compound which gives an ultraviolet-ray absorption effect to the external composition for skin of the present invention.

As (a) the ultraviolet-ray absorber, there may be mentioned 2-ethylhexyl paramethoxycinnamate, phenylbenzimidazole sulfonic acid, isopropyl methoxycinnamate, octyl methoxycinnamate, para-aminobenzoic acid, ethyl PABA, ethyl-dihydroxypropyl PABA, ethylhexyl-dimethyl PABA, homosalate, ethylhexyl salicylate, 3-benzylidene camphor, 4-methylbenzylidene camphor, benzylidene camphor sulfonic acid, camphor benzalkonium methosulfate, polyacrylamidomethyl benzylidene camphor, diethylhexyl butamidotriazone, octyl triazone, disodium phenyl dibenzimidazole tetrasulfonate, a polyorganosiloxane having a benzalmalonate functional group, etc., which are B wave (UV-B) absorbers; 4-tert-butyl-4-methoy-benzoylmethane, hexyl 2-[4-(diethylamino)-2-hydroxybenzoyl]benzoate, 2-(2'-hydroxy-5'-methylphenyl)benzotriazole, 2-[4,6-bis(2,4-dimethylphenyl)-1,3,5-triazin-2-yl]-5-[(octyl)oxy]-phenol, 2-ethylhexyl dimethoxybenzylideneoxoimidazolidine propionate, etc., which are A wave (UV-A) absorbers; and 6-(4-methoxyphenyl)-1,3,5-triazine, tetrahydroxybenzophenone, 2-hydroxy-4-methoxybenzophenone, 2,4-bis-[{4-(2-ethylhexyloxy)-2-hydroxy}-phenyl]drometrizole trisiloxane, 2,2'-methylenebis[6-(2H-benzotriazole-2-yl)-4-(1,1,3,3-tetramethylbutyl)phenol], octocrylene, etc., which are AB wave absorbers, and the like. As (a) the ultraviolet-ray absorber, the above-mentioned ultraviolet-ray absorbers may be contained a single kind alone or may be contained two or more kinds.

Among these, as the ultraviolet-ray absorber contained in the external composition for skin of the present invention, from the viewpoint that a strengthening effect of ultraviolet-ray absorbability by (b) the inorganic phosphor can be easily obtained, it is preferred that at least one kind of a B wave (UV-B) absorbent (the ultraviolet-ray absorber which absorbs UVB) is contained, and more preferably 2-ethylhexyl paramethoxycinnamate is contained. It is also preferred that 2-ethylhexyl paramethoxycinnamate, and hexyl 2-[4-(diethylamino)-2-hydroxybenzoyl]benzoate or 6-(4-methoxyphenyl)-1,3,5-triazine are formulated in combination.

When the ultraviolet-ray absorbing component is formulated, an amount thereof to be used may be optionally selected in consideration with a feeling of use to a skin or an effect thereof, and it is, for example, 0.01 to 20% by mass, preferably 0.1 to 15% by mass based on the whole external composition for skin of the present invention.

<(b) Inorganic Phosphor>

In the external composition for skin of the present invention, an ultraviolet-ray absorption effect by (a) the ultraviolet-ray absorber can be markedly enhanced by containing (b) the inorganic phosphor.

(b) The inorganic phosphor preferably comprises an activation type phosphor comprising a base material and an activator. As the base material, a metal oxide, a metal sulfide, a metal sulfate or a halophosphoric acid compound, etc., may be used and as the activator, manganese, europium, cerium, praseodymium, lanthanum, gadolinium, terbium, dysprosium, holmium, erbium, thulium, yttrium, iron, zinc, etc., may be used.

As (b) the inorganic phosphor, there may be mentioned a red phosphor such as $CaAl_{12}O_{19}:Mn^{4+}$, $CaAl_{12}O_{19}:Cr^{3+}$, $Ca_3Al_2O_6:Eu^{3+}$, $Ca_3(PO_4)_2:Mn$, $NaCl:Mn$, $Mg_2TiO_4:Mn$, $MnCl_2$, etc., and a blue phosphor such as $CaAl_2O_4:Eu^{2+}$, $Ca_{12}Al_{14}O_{33}:Ce^{3+}$, etc., and in the viewpoint of strengthening the ultraviolet-ray absorption effect of the external composition for skin of the present invention, aluminate phosphor is preferred, and an alkaline earth metal aluminate phosphor is more preferred.

As (b) the inorganic phosphor, calcium aluminate in which manganese or europium is activated is further preferred, and calcium manganese aluminate in which manganese is activated represented by the following formula (1);

$$Ca_XAl_YO_{(2X+3Y+4Z)/2}:Mn^{4+}_Z \qquad (1)$$

is particularly preferred.

In the formula, $0.1<X<1.05$, $11.9<Y\leq12$ and $0.0005<Z<0.1$.

The compound represented by the above-mentioned formula (1) is a compound in which $Mn^{4+}$ is doped to the compound represented by the formula $Ca_XAl_YO_{(2X+3Y+4Z)/2}$. $CaAl_{12}O_{19}:Mn^{4+}$ is a red phosphor developed in 1971 (for example, see A. Bergstein et al, "Manganese-Activated Luminescence in Sr Al12 O19 and Ca Al12 O19" J. Electrochem. Soc., 118, p. 116 (1971)). It has been reported that it shows red light-emission at around 657 nm by replacing an octahedral site of $CaAl_{12}O_{19}$ with $Mn^{4+}$. Although this red phosphor has been researched and developed as a red phosphor for a white LED in recent years, no investigation has been made for formulating it into an external composition for skin.

The present inventors have found that the above-mentioned red phosphor is a safe material that does not adversely affect human health when it is used as a material of the external composition for skin, further safety of which is high, and exhibits an effect of markedly enhance the ultraviolet-ray absorption effect of (a) the ultraviolet-ray absorber. In addition, since it shows red light emission upon receiving the ultraviolet-ray, by using the external composition for skin of the present invention, not only sunscreen effect can be obtained but also coloration of the skin is improved, and further, the emitted red light can increase gene expression of the vasodilator, and it can be expected to have an effect to improve skin blood flow and improve facial color.

X, Y and Z in the above-mentioned formula (1) satisfy that, in the viewpoint that the effect of the above-mentioned present invention is excellent, X is more preferably a number exceeding 0.9 and less than 1.0. Z is more preferably a number exceeding 0.001 and less than 0.05.

The particle size of (b) the inorganic phosphor is preferably 1 μm to 100 μm, more preferably 1 to 50 μm, and particularly preferably 1 to 20 μm. By setting the particle size within the above range, the feeling of use of the external composition for skin of the present invention can be made excellent. The particle size is an average value of the values measured optional 250 particles in an image from the 1,000-fold image using a scanning type electron microscope (JSM840F manufactured by JOEL Ltd.). The particle size is a value measured with reference to the major axis of the particle.

(b) The inorganic phosphor is preferably an inorganic phosphor having a main wavelength in the region of 600 to 750 nm since it can be expected the effects that the red light emitted can increase gene expression of the vasodilator, improve the blood flow of the skin and make the face color good in addition to making the color of the skin good.

A process for producing (b) the inorganic phosphor is not particularly limited, and can be obtained by, for example, mixing a compound such as an alkaline earth metal, etc., an aluminum-source compound, a compound corresponding to the doped ion (for example, a manganese-source compound), which are starting materials, with a ratio corresponding to the molar ratio of the objective compound to form a precursor, and then, subjecting to firing.

As a method for mixing these starting compounds, the conventionally known method can be used. For example, there may be mentioned a method in which the starting compounds are made an aqueous dispersion, mixed by stirring or pulverizing using a wet media mill, and then, the whole mixture is dried by evaporation, and a method in which the starting compounds are mixed in a dry system using a general mixing device such as a Henschel mixer, a tumbler, etc., a hammer mill or a high-pressure air jet mill, or a combination thereof, etc.

As a method for firing, the conventionally known method can be used, and it may be, for example, a method in which firing is carried out by using a crucible made of ceramics, or a method in which firing is carried out while rotating by using a rotary kiln.

(b) The inorganic phosphor can be formulated as it is, in the external composition for skin and if necessary, it may be formulated after subjecting to various surface treatment by the conventionally known method.

Also, these surface treatments may be carried out one kind alone, or may be carried out the several kinds with laminated or mixed treatment.

The external composition for skin of the present invention preferably contains (b) the inorganic phosphor in a ratio of 0.1 to 15% by mass, more preferably 0.1 to 10% by mass. In addition, a formulation ratio (mass ratio) of (a) the ultraviolet-ray absorber and (b) the inorganic phosphor is preferably 100:1 to 1:100, more preferably 10:1 to 1:10. By containing (b) the inorganic phosphor with the above-mentioned ratio in the external composition for skin of the present invention, ultraviolet-ray absorbability can be more improved.

<Other Components>

The external composition for skin of the present invention may contain, in addition to the above-mentioned essential components, depending on the various purposes, other components such as inorganic particles other than (b) the inorganic phosphor, oils, a lipophilic nonioinic surfactant, a hydrophilic nonioinic surfactant, other surfactants, a sequestering agent, a natural water-soluble polymer, a semisynthetic water-soluble polymer, a synthetic water-soluble polymer, an inorganic water-soluble polymer, various kinds of extracts, various kinds of powders, a moisturizing ingredient, a polyhydric alcohol, a scrubbing agent, an ultraviolet-ray scattering component, a convergent component, a peptide or a derivative thereof, an amino acid or a derivative thereof, a cleaning component, a horny softening component, a cell activating component, an antiaging component, a blood circulation promoting component, a whitening component, a component having a preventive and/or repairing effect on DNA damage, an antiinflammatory component, an antioxidative component, Vitamins, a sebum adsorbing component, an antimicrobial component, etc., within the range which does not impair the effect of the present invention. In the external composition for skin of the present invention, these components may be formulated a single kind alone, or two or more kinds in combination. These respective components are not particularly limited as long as they can be used in the fields of pharmaceuticals, quasi-drugs, cosmetics, etc., and arbitrary ones can be optionally selected and used.

<Producing Method of External Composition for Skin>

A method for producing the external composition for skin of the present invention is not particularly limited, and may be produced by formulating (a) the ultraviolet-ray absorber and (b) the inorganic phosphor which are essential components, and a component(s) optionally selected from the other components, etc., and mixing by the conventional manner.

Use of the external composition for skin of the present invention is not particularly limited and may be used for, for example, a basic cosmetic such as lotion, moisturizing liquid, milky lotion, beauty liquid, pack, hand cream, body lotion and body cream; a cleansing cosmetic such as facial cleanser, makeup remover and body shampoo; a make-up cosmetic such as a foundation and make-up ground (in the basic cosmetic, the cleaning cosmetic and the make-up cosmetic, the sunscreen function (UV cutting function) may be specified explicitly or may not be specified); and a sunscreen cosmetic, etc. In addition, there may be mentioned a multifunctional type preparation in which the functions of these preparations are combined into one preparation. These preparations can be produced according to the conventional manner.

EXAMPLES

In the following, the present invention is explained in more detail by referring to Examples, but the present invention is not limited by these Examples. Incidentally, the unit of the numerical values in the respective Tables is % by mass otherwise specifically mentioned.

[Preparation of External Composition for Skin]

(1) Production of Inorganic Particles Containing Aluminate Phosphor (Calcium Manganese Aluminate) and Titanate Phosphor (Magnesium Manganese Titanate)

In water were charged 4.97 g of calcium carbonate (CWS-20 available from Sakai Chemical Industry, Co., Ltd.), manganese carbonate (0.06 g available from Chuo Denki), 32.0 g of aluminum oxide (RA-50 available from Sumitomo Chemical Industry Co., Ltd.) and 0.18 g of calcium fluoride (first class grade reagent, available from Wako Pure Chemical Industries, Ltd.) as a flux component, and 70.15 g of magnesium fluoride (special grade reagent, available from Wako Pure Chemical Industries, Ltd.), and the mixture was sufficiently mixed by using a planetary ball mill at 250 rpm for 30 minutes. The mixed slurry was dried by evaporation at 130° C. and the resulting solid material was crushed in a mortar to obtain firing precursor powder. Then, 15 g of the firing precursor was filled in a crucible made of alumina, and a temperature thereof was raised up to 1,600° C. with 200° C./hour in an ambient atmosphere, maintained at that state for 3 hours and then lowered to room temperature with 200° C./hour. The obtained fired product was crushed in a mortar to produce inorganic particles containing aluminate phosphor. Also, the titanate phosphor (magnesium manganese titanate) was produced in accordance with the production method of the above-mentioned aluminate phosphor.

(2) Preparation of External Composition for Skin

According to the prescriptions described in the following Tables 1 to 5, the external compositions for skin of Examples 1 to 6 and Comparative examples 1 to 7 were prepared according to the conventional manner. The following test was carried out with regard to the respective external compositions for skin, and evaluated.

TABLE 1

| Name of component | Formulation amount (%) | | |
|---|---|---|---|
| | Comparative example 1 | Comparative example 2 | Example 1 |
| Purified water | 93 | 95 | 90 |
| (Hydroxyethyl acrylate/acryloyl dimethyl taurine Na) copolymer (*1) | 2 | 2 | 2 |
| 2-Ethylhexyl paramethoxycinnamate (*2) | 5 | 0 | 5 |
| Calcium manganese aluminate | 0 | 3 | 3 |
| Total | 100 | 100 | 100 |

(*1) Simulgel NS (SEPPIC Co.)
(*2) Ubinul MC80 (BASF)

TABLE 2

| Name of component | Formulation amount (%) | |
|---|---|---|
| | Comparative example 3 | Example 2 |
| Purified water | 86 | 83 |
| (Hydroxyethyl acrylate/acryloyl dimethyl taurine Na) copolymer (*1) | 2 | 2 |
| Glyceryl tri(2-ethylhexanoate) | 10 | 10 |
| Hexyl 2-[4-(diethylamino)-2-hydroxybenzoyl]benzoate (*2) | 2 | 2 |
| Calcium manganese aluminate | 0 | 3 |
| Total | 100 | 100 |

(*1) Simulgel NS (SEPPIC Co.)
(*2) Ubinul A Plus Granular (BASF)

TABLE 3

| Name of component | Formulation amount (%) | |
|---|---|---|
| | Comparative example 4 | Example 3 |
| Purified water | 93 | 93 |
| (Hydroxyethyl acrylate/acryloyl dimethyl taurine Na) copolymer (*1) | 2 | 2 |
| Mixed solution of Hexyl 2-[4-(diethylamino)-2-hydroxybenzoyl]benzoate and 2-ethylhexyl paramethoxycinnamate (35:65 in mass ratio) (*2) | 5 | 5 |
| Calcium manganese aluminate | 0 | 3 |
| Total | 100 | 100 |

(*1) Simulgel NS (SEPPIC Co.)
(*2) Ubinul A Plus B (BASF)

TABLE 4

| Name of component | Formulation amount (%) | |
|---|---|---|
| | Comparative example 5 | Example 4 |
| Purified water | 93 | 90 |
| (Hydroxyethyl acrylate/acryloyl dimethyl taurine Na) copolymer (*1) | 2 | 2 |
| 2-Ethylhexyl paramethoxycinnamate (*2) | 5 | 5 |
| Magnesium manganese titanate | 0 | 3 |
| Total | 100 | 100 |

(*1) Simulgel NS (SEPPIC Co.)
(*2) Ubinul MC80 (BASF)

TABLE 5

| Name of component | Formulation amount (%) | | | |
|---|---|---|---|---|
| | Comparative example 6 | Example 5 | Comparative example 7 | Example 6 |
| Purified water | 86 | 83 | 86 | 83 |
| Glyceryl tri-2-ethylhexanoate (*1) | 10 | 10 | 10 | 10 |
| 6-(4-Methoxypheny)-1,3,5-triazine (*2) | 2 | 2 | 0 | 0 |
| 4-tert-Butyl-4'-memoxy-dibenzoylmethane (*3) | 0 | 0 | 2 | 2 |
| (Hydroxyethyl acrylate/acryloyl dimethyl taurine Na) copolymer (*4) | 2 | 2 | 2 | 2 |
| Calcium manganese aluminate | 0 | 3 | 0 | 3 |
| Total | 100 | 100 | 100 | 100 |

TABLE 5-continued

| | Formulation amount (%) | | | |
|---|---|---|---|---|
| Name of component | Comparative example 6 | Example 5 | Comparative example 7 | Example 6 |
| (*1) MYRITOL GTEH (Cognis Japan Co.) | | | | |
| (*2) TINOSORB S (Ciba-Geigy AG) | | | | |
| (*3) Parsol 1789 (DSM Nutrition Japan K.K.) | | | | |
| (*4) Simulgel NS (SEPPIC Co.) | | | | |

<Ultraviolet Rays Absorbability Test>

Figure 2:
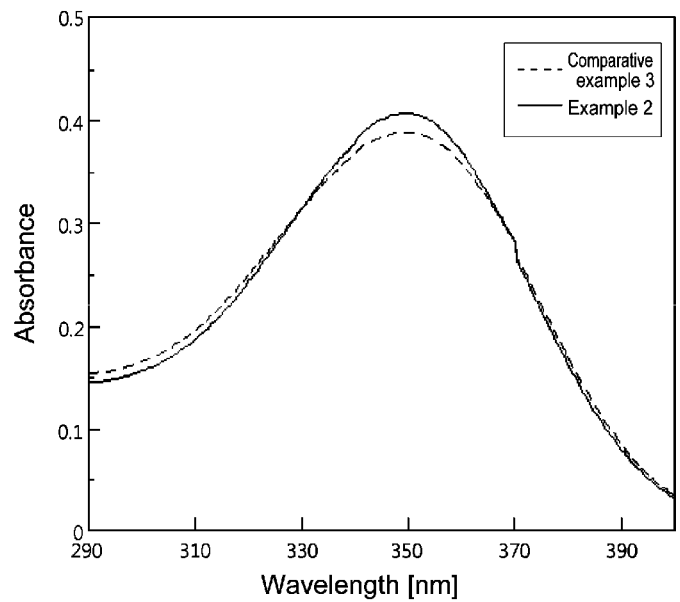
FIG. 2 is a drawing showing ultraviolet-ray absorbability of the external composition for skin which is an embodiment of the present invention.
Figure 3:
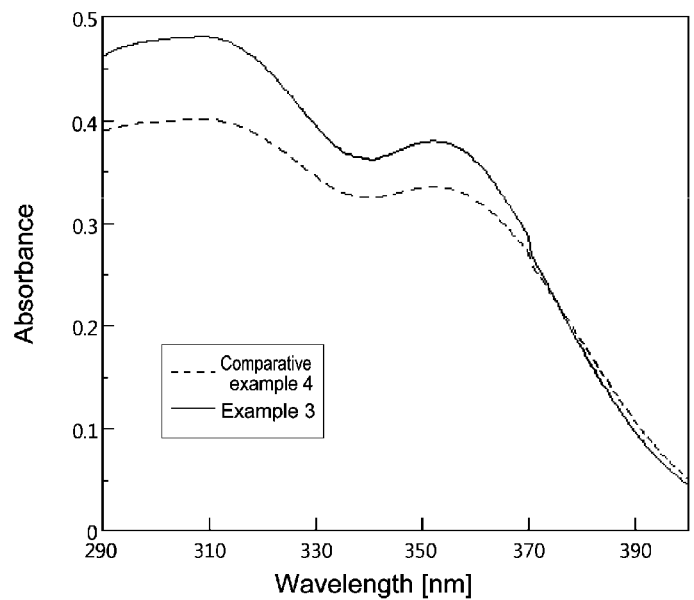
FIG. 3 is a drawing showing ultraviolet-ray absorbability of the external composition for skin which is an embodiment of the present invention.
Figure 4:
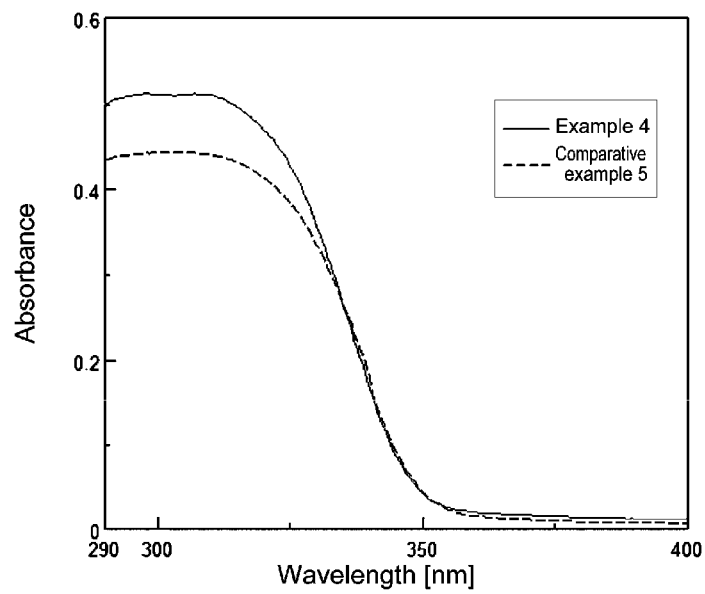
FIG. 4 is a drawing showing ultraviolet-ray absorbability of the external composition for skin which is an embodiment of the present invention.

The respective external compositions for skin were uniformly coated on a PMMA plate so that these became 1.3 mg/cm$^2$, and after drying for 15 minutes, UV spectrum thereof was measured by an ultraviolet visible light spectrophotometer V-650 (manufactured by JASCO Corporation). The results corresponding to Table 1 is shown in FIG. 1, the results corresponding to Table 2 is shown in FIG. 2, the results corresponding to Table 3 is shown in FIG. 3, the results corresponding to Table 4 is shown in FIG. 4, and the results corresponding to Table 5 is shown in FIG. 5.

It could be understood that ultraviolet-ray absorbability of the external composition for skin of Example 1 containing 2-ethylhexyl paramethoxy-cinnamate which is the ultraviolet-ray absorber (UV-B) and aluminate phosphor (calcium manganese aluminate) was markedly enhanced as compared with that of the external composition for skin of Comparative example 1 containing 2-ethylhexyl paramethoxycinnamate alone. Incidentally, ultraviolet-ray absorbability could scarcely be admitted only by the aluminate phosphor (Comparative example 2). Also, in the external composition for skin of Example 2 containing hexyl 2-[4-(diethylamino)-2-hydroxybenzoyl]benzoate which is the ultraviolet-ray absorber (UV-A), when aluminate phosphor (calcium manganese aluminate) was formulated thereto, enhancement of ultraviolet-ray absorbability could be admitted as compared to that of the external composition for skin of Comparative example 3 containing hexyl 2-[4-(diethylamino)-2-hydroxybenzoyl]benzoate alone. On the other hand, the external composition for skin of Example 3 containing a mixed solution of hexyl 2-[4-(diethylamino)-2-hydroxybenzoyl]benzoate and 2-ethylhexyl paramethoxycinnamate which are the ultraviolet-ray absorbers (UV-A and B) and aluminate phosphor (calcium manganese aluminate) was found to be markedly enhanced in ultraviolet-ray absorbability as compared with that of the external composition for skin of Comparative example 4 containing hexyl 2-[4-(diethylamino)-2-hydroxybenzoyl]-benzoate and 2-ethylhexyl paramethoxycinnamate. Further, in the external composition for skin of Example 4 in which the aluminate phosphor to be used in combination with 2-ethylhexyl paramethoxycinnamate which is the ultraviolet-ray absorber (UV-B) was substituted with magnesium manganese titanate, it could be understood that the ultraviolet-ray absorbability thereof was markedly enhanced as compared with that of the external composition for skin of Comparative example 5 containing no magnesium manganese titanate (FIG. 4). Moreover, the external composition for skin of Example 5 containing 6-(4-methoxyphenyl)-1,3,5-triazine and aluminate phosphor (calcium manganese aluminate) which is the ultraviolet-ray absorber (UV-AB) was found to be markedly enhanced in ultraviolet-ray absorbability as compared with that of the external composition for skin of Comparative example 6 containing 6-(4-methoxyphenyl)-1,3,5-triazine alone. Furthermore, the external composition for skin of Example 6 containing 4-tert-butyl-4-methoxybenzoyl-methane which is the ultraviolet-ray absorber (UV-A) and aluminate phosphor (calcium manganese aluminate) was found to be markedly enhanced in ultraviolet-ray absorbability as compared with that of the external composition for skin of Comparative example 7 containing 4-tert-butyl-4-methoxybenzoyl-methane alone.

<Measurement of Gene Expression Amount of Vasodilator>

Calcium manganese aluminate emits red light (wavelength: 660 nm) upon receiving ultraviolet-ray (excitation wavelength: 365 nm). Normal human vascular endothelial cells were irradiated with red light at an irradiation intensity of 0 to 1.32 J/cm$^2$. Gene expression of vascular endothelial type Nitric Oxide Synthase (NOS3) which is a vasodilator was confirmed by the qRT-PCR method at the time of 24 hours after the irradiation. It was compared by making the expression amount under the non-irradiated conditions 1. For the respective conditions, the experimentswere carried out with n=3. The results are shown in FIG. 6.

Figure 6:
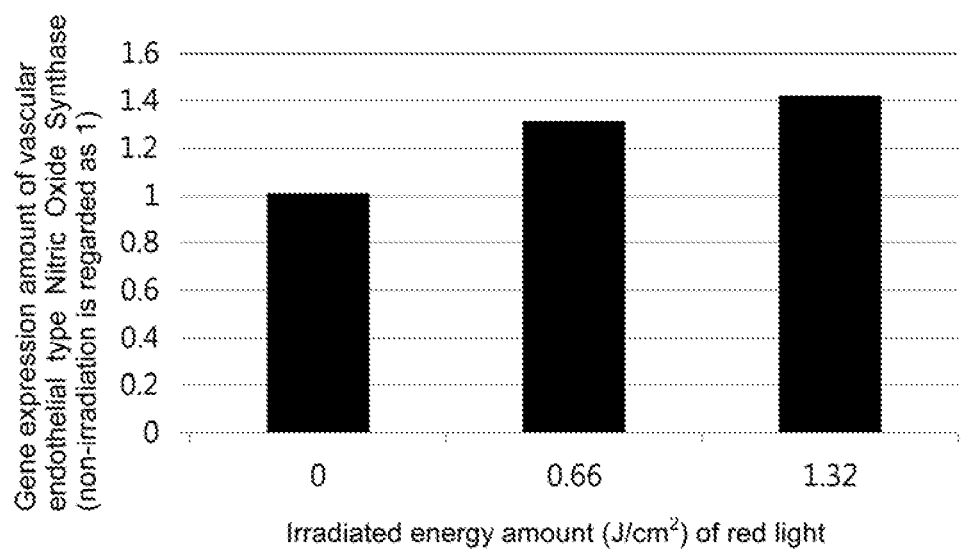
FIG. 6 is a drawing showing a gene expression promotion effect of a vasodilator by red light irradiation.

As shown in FIG. 6, it could be confirmed that the gene expression amount of the vasodilator in vascular endothelial cells was increased depending on irradiation intensity by irradiating the red light.

The invention claimed is:

1. An external composition for skin, which composition comprises
   (a) an ultraviolet-ray absorber and
   (b) a calcium manganese aluminate phosphor having the formula

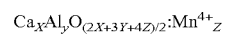
   $Ca_XAl_YO_{(2X+3Y+4Z)/2}:Mn^{4+}{}_Z$ wherein $0.1<X<1.05$, $11.9<Y<12$ and $0.0005<Z<0.1$
   and/or
   an alkaline earth metal titanate phosphor.
2. The external composition for skin according to claim 1, wherein (a) the ultraviolet-ray absorber contains at least one kind of an ultraviolet-ray absorber which absorbs UVB.
3. The external composition for skin according to claim 1, wherein (a) the ultraviolet-ray absorber is at least one kind of an ultraviolet-ray absorber selected from the group consisting of
   2-ethylhexyl paramethoxycinnamate,
   phenylbenzimidazole sulfonic acid,
   isopropyl methoxycinnamate,
   octyl methoxycinnamate,
   para-amino-benzoic acid,
   ethyl PABA,
   ethyl-dihydroxypropyl PABA,
   ethylhexyl-dimethyl PABA,
   homosalate,
   ethylhexyl salicylate,
   3-benzylidene camphor,
   4-methylbenzylidene camphor,
   benzylidene camphor sulfonic acid,
   camphor benzalkonium methosulfate,
   polyacrylamidomethyl benzylidene camphor,
   diethylhexyl butamidotriazone,
   octyl triazone,
   disodium phenyl dibenzimidazole tetrasulfonate,
   a polyorganosiloxane having a benzalmalonate functional group,
   4-tert-butyl-4-methoxybenzoylmethane,
   hexyl 2-[4-(diethylamino)-2-hydroxybenzoyl]benzoate,
   2-(2'-hydroxy-5'-methyl-phenyl)benzotriazole,
   2-[4,6-bis(2,4-dimethylphenyl)-1,3,5-triazin-2-yl]-5-[(octyl)oxy]-phenol, 2-ethylhexyl dimethoxybenzylideneoxoimidazolidine propionate,
6-(4-methoxyphenyl)-1,3,5-triazine,
tetrahydroxybenzophenone,
2-hydroxy-4-methoxy-benzophenone,
2,4-bis-[{4-(2-ethylhexyloxy)-2-hydroxy}-phenyl]-drometrizole trisiloxane,
2,2'-methylenebis[6-(2H-benzotriazole-2-yl)-4-(1,1,3,3-tetramethyl-butyl)phenol] and octocrylene.

4. The external composition for skin according to any one of claims 1 to 3, wherein (a) the ultraviolet-ray absorber contains 2-ethylhexyl paramethoxycinnamate.

5. The external composition for skin according to any one of claims 1 to 3, wherein (a) the ultraviolet-ray absorber contains 2-ethylhexyl paramethoxycinnamate and hexyl 2-[4-(diethylamino)-2-hydroxybenzoyl]benzoate.

6. The external composition for skin according to any one of claims 1 to 3, wherein a content of (b) the inorganic phosphor is 0.1 to 10% by mass based on the whole external composition for skin.

7. The external composition for skin according to any one of claims 1 to 3, wherein it is a sunscreen composition.

* * * * *